(12) United States Patent
Litvak et al.

(10) Patent No.: US 11,285,322 B2
(45) Date of Patent: Mar. 29, 2022

(54) CHANNEL SELECTION SYSTEMS AND METHODS THAT UTILIZE FINE STRUCTURE INFORMATION

(71) Applicant: ADVANCED BIONICS AG, Staefa (CH)

(72) Inventors: Leonid M. Litvak, Los Angeles, CA (US); Nobutaka Okuyama, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 260 days.

(21) Appl. No.: 16/304,682

(22) PCT Filed: May 31, 2016

(86) PCT No.: PCT/US2016/035119
§ 371 (c)(1),
(2) Date: Nov. 26, 2018

(87) PCT Pub. No.: WO2017/209742
PCT Pub. Date: Dec. 7, 2017

(65) Prior Publication Data
US 2020/0188669 A1 Jun. 18, 2020

(51) Int. Cl.
*A61N 1/02* (2006.01)
*A61N 1/36* (2006.01)
*A61N 1/372* (2006.01)

(52) U.S. Cl.
CPC ......... *A61N 1/36039* (2017.08); *A61N 1/025* (2013.01); *A61N 1/37252* (2013.01)

(58) Field of Classification Search
CPC ............... A61N 1/36039; A61N 1/025; A61N 1/37252; A61N 1/36038
See application file for complete search history.

(56) References Cited

U.S. PATENT DOCUMENTS 6,594,525 B1 7/2003 Zierhofer
7,751,900 B2 7/2010 Voelkel
(Continued)

FOREIGN PATENT DOCUMENTS

EP 2207592 7/2010
WO 2016/057016 4/2016

OTHER PUBLICATIONS

International Search Report and Written Opinion received in International Application No. PCT/US16/035119, dated Mar. 6, 2017.
(Continued)

*Primary Examiner* — Ankit D Tejani
*Assistant Examiner* — Joshua Brendon Solomon
(74) *Attorney, Agent, or Firm* — ALG Intellectual Property, LLC (57) ABSTRACT

An exemplary sound processor 1) divides an audio signal into M analysis channels, 2) generates M fine structure signals corresponding to the M analysis channels, wherein each fine structure signal included in the M fine structure signals represents fine structure information for a different analysis channel included in the M analysis channels, and 3) selects, based on the M fine structure signals, only N analysis channels included in the M analysis channels for presentation to the patient during a stimulation frame, wherein N is less than M. Corresponding systems and methods are also disclosed.

17 Claims, 9 Drawing Sheets

(56) References Cited

U.S. PATENT DOCUMENTS

| | | |
|---|---|---|
| 2009/0125082 A1 | 5/2009 | Schleich |
| 2011/0004274 A1 | 1/2011 | Schleich et al. |
| 2014/0064532 A1* | 3/2014 | Litvak ................ A61N 1/36038 |
| | | 381/326 |
| 2015/0080980 A1 | 3/2015 | Meister et al. |
| 2017/0246457 A1* | 8/2017 | Litvak .................. A61N 1/0541 |

OTHER PUBLICATIONS

Buechner, A. et al., Clinical evaluation of cochlear implant sound coding taking into account conjectural masking functions, MP3000, Cochlear Implants International, 2011; vol. 12, No. 4: 194-204.

Neben, N. et al., New cochlear implant research coding strategy based on the MP3000 strategy to reintroduce the virtual channel effect, Acta Oto-Laryngologica, 2013; 133:481-490.

Nogueira, et al., Signal Processing Strategies for Cochlear Implants Using Current Steering, EURASIP Journal on Advances in Signal Processing, 2009.

Vandali, et al., Development of a Temporal Fundamental Frequency Coding Strategy for Cochlear Implants, J. Acoust.Soc. Am., Mar. 13, 2011.

Vandali, et al., Speech Perception as a Function of Electrical Stimulation Rate: Using the Nucleus 24 Cochlear Implant System, Ear & Hearing, 2000, pp. 608-624.

\* cited by examiner

CHANNEL SELECTION SYSTEMS AND METHODS THAT UTILIZE FINE STRUCTURE INFORMATION

BACKGROUND INFORMATION

Various N-of-M channel selection strategies for cochlear implant systems have been described in which a cochlear implant system only stimulates a subset of the available electrodes in each given stimulation frame. In these N-of-M channel selection strategies, a cochlear implant system divides an incoming audio signal into M analysis channels (or simply "channels") and then presents only N analysis channels to the patient (e.g., by applying electrical stimulation representative of the signals contained within the N analysis channels by way of a plurality of intracochlear electrodes that correspond to the N analysis channels).

Many conventional N-of-M channel selection strategies are energy-based. For example, a cochlear implant system operating in accordance with a conventional N-of-M channel selection strategy may select only the N analysis channels with the highest energy (e.g., highest amplitude) signals for presentation to a patient during a particular stimulation frame. This means that information included in the non-selected (i.e., lower energy) channels is not conveyed to the patient during that particular stimulation frame. Unfortunately, for reasons that will be described herein, an N-of-M channel selection strategy that is solely energy-based may not be the most effective or efficient for a cochlear implant system that incorporates fine structure information into an electrode firing pattern utilized by the cochlear implant system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Channel selection systems and methods that utilize fine structure information are described herein. As will be described below, an exemplary sound processor included in a cochlear implant system associated with a patient may 1) divide an audio signal into M analysis channels, 2) generate M fine structure signals corresponding to the M analysis channels, wherein each fine structure signal included in the M fine structure signals represents fine structure information for a different analysis channel included in the M analysis channels, and 3) select, based on the M fine structure signals, only N analysis channels included in the M analysis channels for presentation to the patient during a stimulation frame, wherein N is less than M. In some examples, the sound processor may also generate M energy signals (e.g., M envelope signals) corresponding to the M analysis channels. In these examples, the selection of the N analysis channels for presentation to the patient during a stimulation frame may be based on both the M fine structure signals and the M energy signals.

Because the N-of-M channel selection strategies described herein are based at least in part on the fine structure signals corresponding to each of the M analysis channels, the systems and methods described herein may optimize performance of a cochlear implant system that incorporates fine structure information into an electrode firing pattern utilized by the cochlear implant system. As used herein, "fine structure information" includes information contained in a waveform of a signal (e.g., an incoming audio signal detected by the cochlear implant system) other than the envelope of the signal, and may be represented by relatively fast amplitude fluctuations in the waveform. Delivery of fine structure information to a cochlear implant patient (e.g., by incorporating the fine structure information into the electrode firing pattern utilized by the cochlear implant system) may, for example, facilitate enhanced perception by the patient of temporal pitch (e.g., musical and/or vocal pitch), assist the patient in determining a spatial location of a source of the audio signal, compensate for low temporal resolution, and/or otherwise improve the listening experience of the patient.

As used herein, an "electrode firing pattern" specifies when stimulation pulses representative of an audio signal are delivered by a cochlear implant system to electrodes that correspond to the M analysis channels in order to present the audio signal to the patient. The electrode firing pattern may affect a patient's perception of various characteristics of an audio signal presented to the patient. For example, by incorporating fine structure information contained within an audio signal into the electrode firing pattern (e.g., by using the fine structure information to determine the electrode firing pattern utilized by a cochlear implant system), a cochlear implant system may enhance the patient's perception of pitch and/or otherwise improve the listening experience of the patient.

Fine structure information may be incorporated into an electrode firing pattern utilized by a cochlear implant system in any suitable manner. For example, with respect to a particular analysis channel, a sound processor may determine a frequency of content included in the analysis channel and generate a pulse train that has the determined frequency. The pulse train may be, for example, a half-wave rectified square wave that alternates between values of one and zero and may be designated as being a fine structure signal corresponding to the analysis channel. This fine structure signal may be combined (e.g., modulated) with a stimulation pulse train that includes stimulation pulses representative of an envelope of a portion of the audio signal that corresponds to the analysis channel. In this manner, the fine structure signal may prevent stimulation pulses from being applied via the one or more electrodes that correspond to the analysis channel during periods of time that correspond to when the fine structure signal is equal to zero. Likewise, the fine structure signal may allow stimulation pulses to be applied via the one or more electrodes that correspond to the analysis channel during periods of time that correspond to when the fine structure signal is equal to one. Another example may be where the pulse train is modulated using a sinusoidal waveform whose frequency and phase corresponds to the fine structure signal. Yet another example may be a more complex waveform that is derived from the fine structure of either the present channel or of other channels.

A conventional N-of-M channel selection strategy that is only energy-based does not take into account the fact that the fine structure signal prevents stimulation pulses from being applied via the one or more electrodes that correspond to the analysis channel during periods of time that correspond to when the fine structure signal is equal to zero. Hence, the conventional N-of-M channel selection strategy that is only energy-based may select the analysis channel for presentation to the patient (if, for example, the energy within the analysis channel is relatively high) during a particular stimulation frame even if the stimulation frame temporally occurs during a time period in which the fine structure signal corresponding to the analysis channel is equal to zero or is substantially less than the envelope signal itself. In other words, the particular analysis channel may be selected for presentation to the patient during a time period that the fine structure signal corresponding to the analysis channel prevents the analysis channel from actually being presented. This may result in less than N channels being presented to the patient during the stimulation frame, which may be an inefficient use of processing resources within the sound processor and which may result in a sub-optimal hearing experience for the patient.

In contrast, by basing the N-of-M channel selection strategies described herein at least in part on fine structure signals that correspond to each of the M analysis channels, the systems and methods described herein may ensure that an analysis channel is not selected for presentation during a stimulation frame that temporally occurs during a time period in which a fine structure signal corresponding to the analysis channel prevents the analysis channel from being presented. This allows an alternative analysis channel to be selected for presentation during the stimulation frame (e.g., in place of the analysis channel that is being prevented from being presented). This, in turn, may optimize efficiency, efficacy, and performance of the cochlear implant system, as well as the listening experience of the patient.

Figure 1:
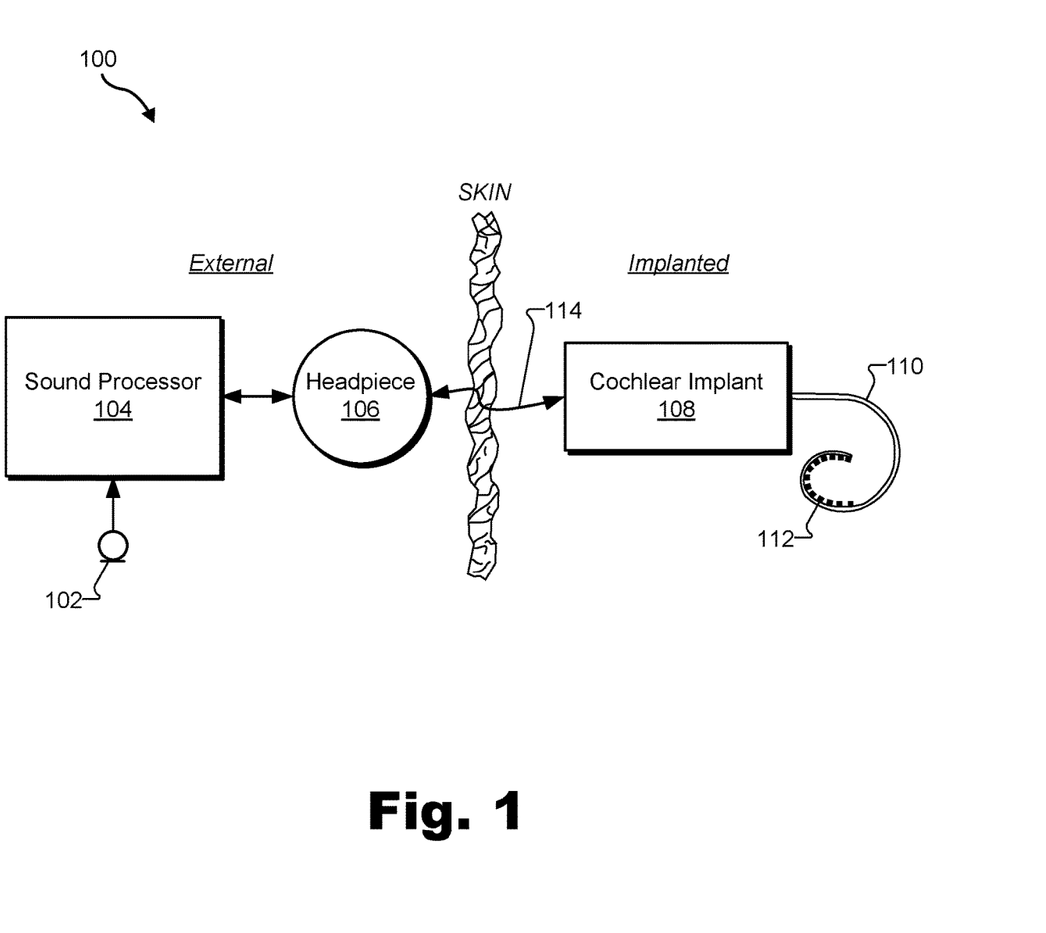
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 (also referred to as an implantable cochlear stimulator) and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
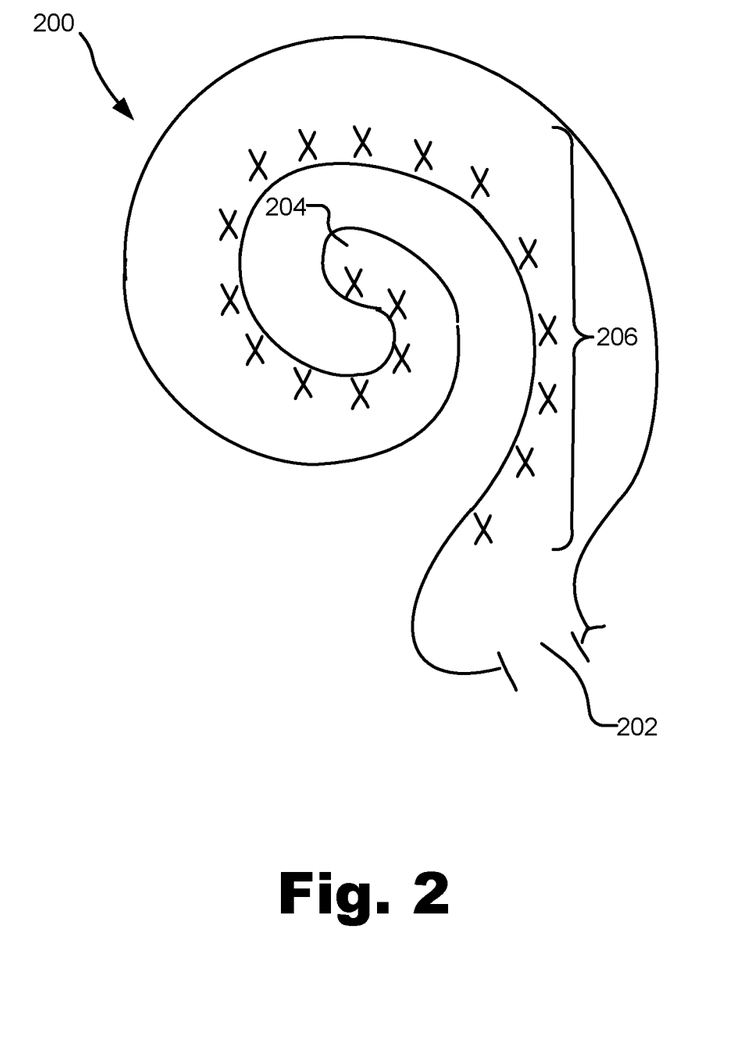
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
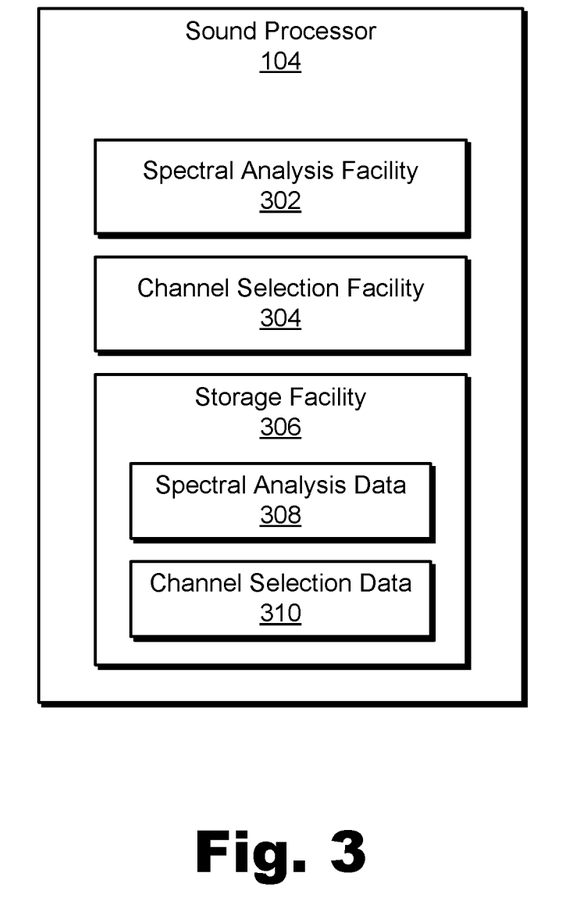
FIG. 3 illustrates exemplary components of a sound processor according to principles described herein.

FIG. 3 illustrates exemplary components included in sound processor 104. As shown, sound processor 104 may include a spectral analysis facility 302, a channel selection facility 304, and a storage facility 306, which may be in communication with one another using any suitable communication technologies. Storage facility 306 may maintain spectral analysis data 308 generated and/or used by spectral analysis facility 302, and channel selection data 310 generated and/or used by channel selection facility 304. Storage facility 306 may maintain additional or alternative data as may serve a particular implementation. One or more of facilities 302-306 may include or be implemented one or more computing devices and/or processors configured to perform one or more of the functions described herein.

Spectral analysis facility 302 may divide an audio signal (e.g., an audio signal presented to the patient and representative of speech, music, and/or other types of sound) into M analysis channels. Each analysis channel includes a signal representative of a distinct portion of the audio signal. As used herein, "M" is an integer and refers to a total number of analysis channels into which an audio signal may be divided. For example, M may be any integer greater than three (e.g., equal to or greater than eight). In some examples, M is equal to the total number of stimulation channels formed by electrodes 112 through which electrical stimulation representative of the audio signal may be applied to the patient.

Spectral analysis facility 302 may divide the audio signal into M analysis channels in any suitable manner. For example, spectral analysis facility 306 may be implemented by a plurality of band-pass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 302 may include one or more components configured to apply a Discrete Fourier Transform (e.g., by way of a Fast Fourier Transform ("FFT")) to the audio signal.

Figure 4:
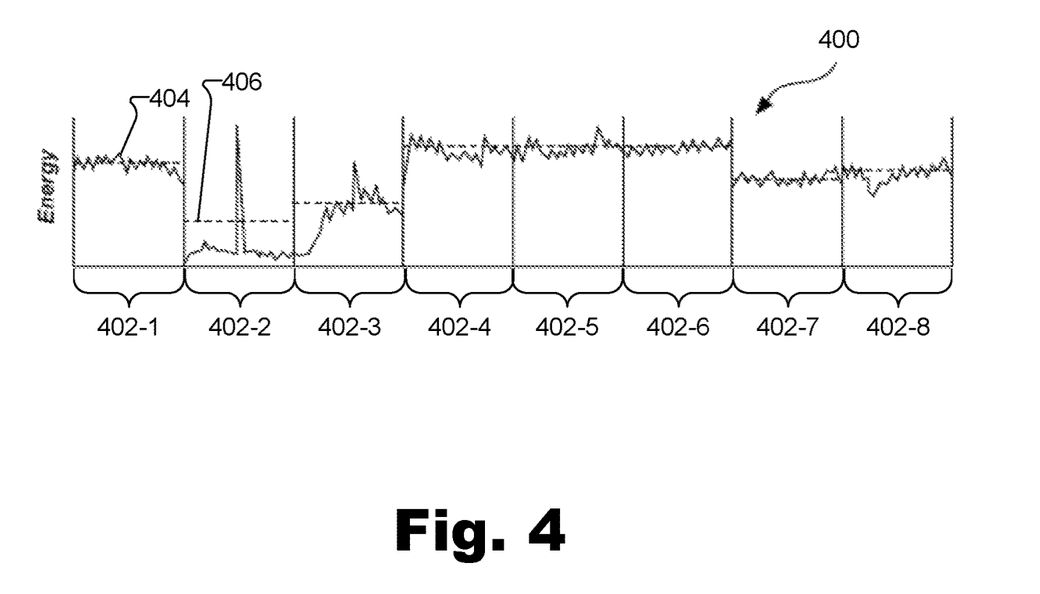
FIG. 4 illustrates an exemplary audio signal in the frequency domain that may be presented to a cochlear implant patient according to principles described herein.

FIG. 4 illustrates an exemplary audio signal 400 in the frequency domain that may be presented to a cochlear implant patient. As shown, the audio signal 400 may be divided by spectral analysis facility 302 into eight analysis channels 402 (e.g., analysis channels 402-1 through 402-8). In this case, M is equal to eight. It will be recognized that audio signal 400 may alternatively be divided into any other number of analysis channels as may serve a particular implementation.

Each analysis channel 402 may correspond to a distinct frequency band, and, as shown, includes a signal (e.g., signal 404) representative of a distinct portion of the audio signal. The vertical axis in FIG. 4 represents the amount of signal energy within each analysis channel 402. As shown in FIG. 4, each analysis channel contains varying energy levels. The average energy level in each analysis channel 402 is represented by a dashed horizontal line. For example, line 406 represents the average energy level included in analysis channel 402-2.

Returning to FIG. 3, channel selection facility 304 may select N analysis channels from the M total analysis channels for presentation to the patient during a stimulation frame. As used herein, "N" is an integer greater than zero and less than M and refers to a total number of analysis channels that are selected for presentation to a patient during a stimulation frame. For example, if M is equal to eight, N may be between one and seven.

As used herein, an analysis channel that has been "selected for presentation" to a patient during a stimulation frame refers to an analysis channel whose signal contained therein will be represented by electrical stimulation applied to the patient during the stimulation frame. In other words, once an analysis channel has been selected for presentation to the patient during the stimulation frame, sound processor 104 (e.g., channel selection facility 304) may direct cochlear implant 108 to apply electrical stimulation representative of the signal contained within the analysis channel to the patient. For example, with reference again to FIG. 4, if analysis channel 402-1 is selected for presentation to the patient during a stimulation frame, sound processor 104 may direct cochlear implant 108 to apply electrical stimulation representative of signal 404 to the patient during the stimulation frame.

As used herein, a "stimulation frame" refers to a period of time during which electrical stimulation representative of the N selected analysis channels is applied to one or more stimulation channels defined by one or more of electrodes 112. During a stimulation session, a plurality of stimulation frames may temporally follow one another. For example, a first stimulation frame, a second stimulation frame, a third stimulation frame, etc. may follow sequentially right after one another as an audio signal is represented to a cochlear implant patient.

Channel selection facility 304 may select the N analysis channels for presentation to the patient in accordance with any suitable N-of-M channel selection strategy. For example, channel selection facility 304 may simply select the N analysis channels that contain the highest average energy levels for presentation to the patient. To illustrate, if N is equal to 4, channel selection facility 304 may select the four analysis channels with the highest average energy levels for presentation to a patient. In the example of FIG. 4, the four analysis channels with the highest average energy levels are channels 402-1, 402-4, 402-5, and 402-6. Hence, these analysis channels would be selected for presentation to the patient. However, as described above, in certain configurations that incorporate fine structure information into the electrode firing pattern, this type of channel selection strategy may result in some analysis channels being selected for presentation during a stimulation frame even though their corresponding fine structure signals will prevent them from actually being presented during the stimulation frame.

Hence, in some examples, channel selection facility 304 may select the N analysis channels for presentation to the patient in accordance with an N-of-M channel selection strategy that utilizes fine structure information. For example, channel selection facility 304 may generate M fine structure signals corresponding to the M analysis channels. Each fine structure signal included in the M fine structure signals represents fine structure information for a different analysis channel included in the M analysis channels. Channel selection facility 304 may then select, based on the M fine structure signals, only N analysis channels included in the M analysis channels for presentation to the patient during a stimulation frame, wherein N is less than M.

Figure 5:
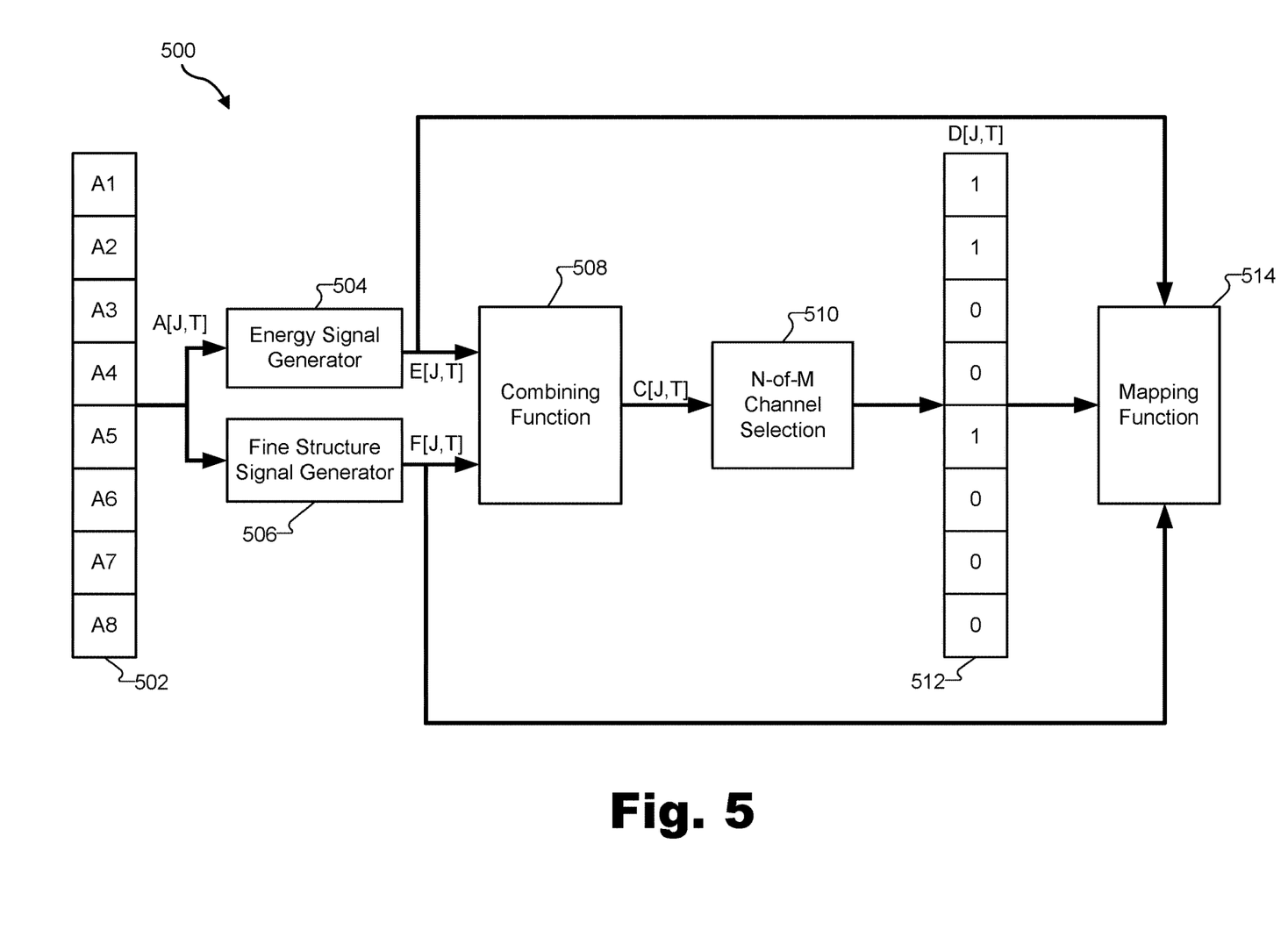
FIG. 5 shows an exemplary implementation of an N-of-M channel selection strategy that utilizes fine structure information according to principles described herein.

To illustrate, FIG. 5 shows an exemplary implementation 500 of an N-of-M channel selection strategy that utilizes fine structure information. As shown, implementation 500 may include a signal array 502, an energy signal generator 504, a fine structure signal generator 506, a combining function block 508, an N-of-M channel selection block 510, a selection state array 512, and a mapping function 514. The various components illustrated in FIG. 5 may be implemented by sound processor 104 (e.g., by channel selection facility 304). In the example of FIG. 5, it will be assumed for illustrative purposes only that there are eight total analysis channels (i.e., that M equals 8) and that the N-of-M channel selection strategy selects five analysis channels for presentation during each stimulation frame (i.e., N equals 5).

Signal array 502 represents individual signals A1 through A8 contained within each of the M analysis channels during any given stimulation frame. Each cell included in signal array 502 corresponds to a different analysis channel. Hence, signal A1 represents a signal contained within a first analysis channel included in the M analysis channels, signal A2 represents a signal contained within a second analysis channel included in the M analysis channels, and so on. Signals A1 through A8 may each include different frequency-band specific portions of an audio signal presented to the patient. For example, signal A1 includes spectral content included in a frequency band associated with the first analysis channel. Signals A1 through A8 may be generated in any suitable way, including any of the ways described above in connection with spectral analysis facility 302. As shown, signal array 502 may be represented mathematically by A[J,T], where J represents the analysis channel number and T represents the stimulation frame.

Energy signal generator 504 may receive the signals included in signal array 502 and, based on the signals included in signal array 502, generate an energy signal corresponding to each of the M analysis channels. The energy signals output by energy signal generator 504 may be represented mathematically as E[J,T], where J represents the analysis channel number and T represents the stimulation frame.

Each energy signal output by energy signal generator 504 may represent an energy level of a signal (i.e., a signal included in signal array 502) included in the energy signal's corresponding analysis channel. For example, an energy signal output by energy signal generator 504 and that corresponds to the first analysis channel represents an energy level of signal A1. This energy level may include an average energy level, a total energy level, a peak energy level, and/or any other measure of energy included in the first analysis channel.

Energy signal generator 504 may generate each energy signal in any suitable way. For example, energy signal generator 504 may be implemented by an envelope detection circuit configured to detect and output envelope signals that are representative of the envelopes of the different analysis channels (i.e., the envelope signals are representative of the envelopes of the signals included in signal array 502). In this implementation, the envelope signals are the energy signals generated by energy signal generator 504.

As shown, fine structure signal generator 506 may also receive the signals included in signal array 502. Fine structure signal generator 506 may, based on the signals included in signal array 502, generate a fine structure signal corresponding to each of the M analysis channels. Each fine structure signal output by fine structure signal generator 506 may represent fine structure information for a particular analysis channel included in the M analysis channels. In other words, each fine structure signal output by fine structure signal generator 506 may represent fine structure information included in a particular signal included in signal array 502. For example, a first structure signal corresponding to the first analysis channel may represent fine structure information included in signal A1. The fine structure signals output by fine structure signal generator 506 may be represented mathematically as F[J,T], where J represents the analysis channel number and T represents the stimulation frame.

Fine structure signal generator 506 may generate each fine structure signal in any suitable way. For example, with respect to a particular analysis channel, fine structure signal generator 506 may determine a frequency that corresponds to the particular analysis channel and generate a pulse train that has the determined frequency. In this example, the pulse train is the fine structure signal corresponding to the particular analysis channel.

Fine structure signal generator 506 may determine a frequency that corresponds to a particular analysis channel in any suitable manner. For example, fine structure signal generator 506 may detect a spectral peak included in the particular analysis channel, identify a frequency of the spectral peak, and designate the identified frequency of the spectral peak as the frequency that corresponds to the particular analysis channel. To illustrate, fine structure signal generator 506 may detect a spectral peak (e.g., the most dominant or highest spectral peak) included in signal A1. Fine structure signal generator 506 may then identify a frequency of the detected spectral peak as being 410 Hz and designate 410 Hz as the frequency that corresponds to the analysis channel that contains signal A1. The frequency of the fine structure signal that corresponds to this analysis channel may then be set to be equal to 410 Hz.

Figure 6:
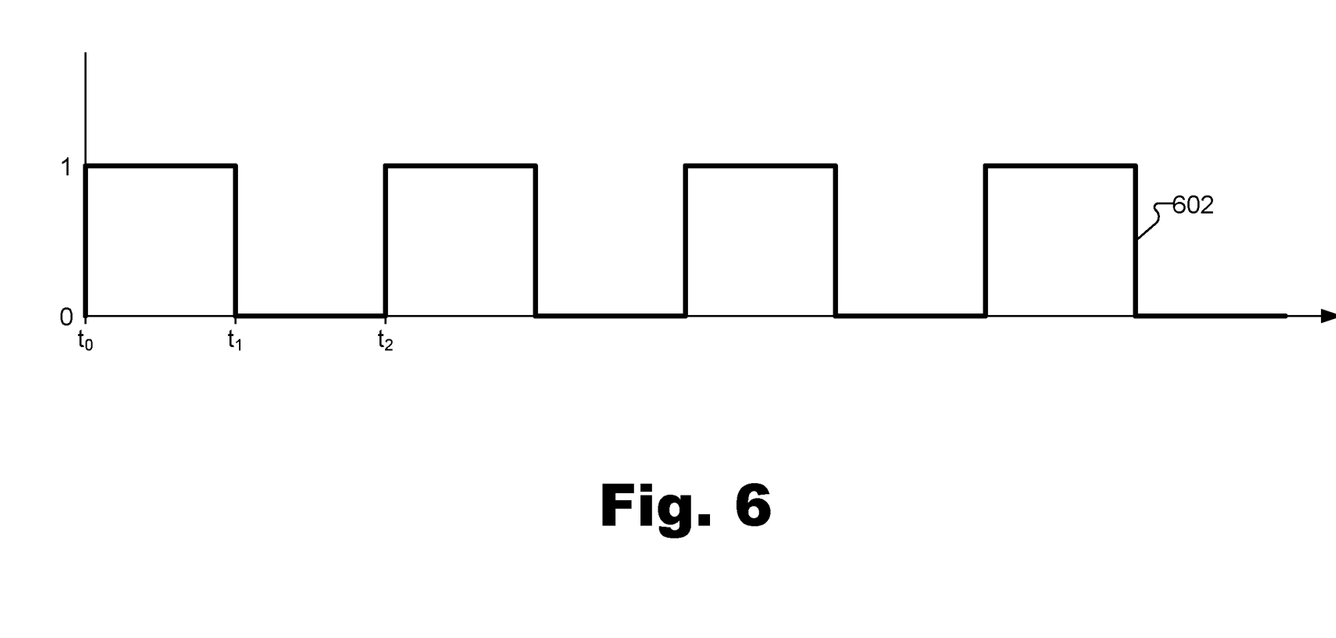
FIG. 6 shows an exemplary fine structure signal according to principles described herein.

FIG. 6 shows an exemplary fine structure signal 602 that may be generated by fine structure signal generator 506 and that may correspond to a particular analysis channel included in the M analysis channels. As shown, fine structure signal 602 includes a half-wave rectified square wave that alternates between values of one and zero. For example, fine structure signal 602 has a value of one between times $t_0$ and $t_1$ and a value of zero between times $t_1$ and $t_2$. While fine structure signal 602 is shown in FIG. 6 to include a half-wave rectified square wave, it will be recognized that fine structure signal 602 may alternatively include any other suitable periodic pulse train as may serve a particular implementation.

As shown, fine structure signal 602 has a period of $t_2-t_0$ and, therefore, a frequency of $1/(t_2-t_0)$. This frequency may be set to be always equal to the determined frequency of the particular analysis channel. For example, if the particular analysis channel in this example contains signal A1, the frequency of fine structure signal 602 may be set by fine structure signal generator 506 to be always equal to the frequency of signal A1 as determined by fine structure signal generator 506. As a particular example, if fine structure signal generator 506 determines that the frequency of signal A1 is 420 Hz, the frequency of fine structure signal 602 may be set to be equal to 420 Hz. As another example, if the frequency of signal A1 subsequently changes to 430 Hz, the frequency of fine structure signal 602 may be accordingly updated to be equal to 430 Hz.

Returning to FIG. 5, fine structure signal generator 506 may be implemented by any suitable component(s). For example, fine structure signal generator 506 may be implemented by a spectral peak locator that determines the frequency corresponding to a particular analysis channel and a carrier synthesis module that generates a pulse train that has the determined frequency. In some examples, the generation of the fine structure signals may additionally or alternatively be based on a predetermined stimulation frame rate associated with the stimulation frame and/or channel numbers of the M analysis channels.

As shown in FIG. 5, energy signals E[J,T] and fine structure signals F[J,T] may be input into combining function 508. Combining function 508 may generate, based on the energy signals E[J,T] and the fine structure signals F[J,T], M selection signals that each have individual values and that each correspond to a different analysis channel included in the M analysis channels. The selection signals generated by combining function 508 may be represented mathematically as C[J,T], where J represents the analysis channel number and T represents the stimulation frame.

Combining function 508 may generate selection signals C[J,T] in any suitable way. For example, with respect to a particular analysis channel, combining function 508 may multiply an energy signal that corresponds to the particular analysis channel with a fine structure signal that corresponds to the particular analysis channel in order to generate a selection signal that corresponds to the particular analysis channel. Because the fine structure signal alternates between one and zero, the selection signal has a value that is equal to the value of the energy signal during time periods where the fine structure signal is equal to one (e.g., during the time period between $t_0$ and $t_1$ in FIG. 6) and a value that is equal to zero during time periods where the fine structure signal is equal to zero (e.g., during the time period between $t_1$ and $t_2$ in FIG. 6).

Combining function 508 may similarly combine the energy signals and fine structure signals that correspond to the other analysis channels. In general, the combination performed by combination function 508 may be mathematically represented by the following equation: C[J,T]=COMB (E[J,T], F[J,T]). The COMB function may be a multiplication function or an addition function or other suitable function. It will be recognized that combining function 508 may alternatively combine the energy signals and fine structure signals in any other suitable manner (e.g., by adding a fine structure signal to an energy signal).

N-of-M channel selection block 510 may receive the selection signals generated by combining function 508 and select, based on the selection signals, N analysis channels for presentation to the patient during the stimulation frame. For example, N-of-M channel selection block 510 may identify the N highest values out of the values of the selection signals generated by combining function 508 and designate the analysis channels that correspond to the N highest values as the N analysis channels that are selected for presentation to the patient during the stimulation frame.

As mentioned above, because the fine structure signals are used to generate the selection signals, the fine structure signals will prevent their corresponding analysis channels from being selected for presentation during a particular stimulation frame if the stimulation frame temporally occurs when the fine structure signals are equal to zero.

N-of-M channel selection block 510 may designate the analysis channels that correspond to the N highest values as the N analysis channels that are selected for presentation to the patient during a stimulation frame in any suitable manner. For example, N-of-M channel selection block 510 may assign a binary value to each analysis channel that indicates whether each analysis channel has been selected for presentation during the stimulation frame.

To illustrate, N-of-M channel selection block 510 may populate selection state array 512 with binary values that indicate whether each analysis channel has been selected for presentation during the stimulation frame. As shown, selection state array 512 includes a plurality of cells or fields that each correspond to a particular analysis channel included in the M analysis channels. In some examples, N-of-M channel selection block 510 may assign a binary value of "1" to an analysis channel if the analysis channel is to be dropped (i.e., not selected for presentation during the stimulation frame). Conversely, N-of-M channel selection block 510 may assign a binary value of "0" to an analysis channel if the analysis channel is to be selected for presentation during the stimulation frame. In the particular example of FIG. 5, there are five "0" values included in selection state array 512, indicating that five analysis channels have been selected for presentation to the patient during the stimulation frame. It will be recognized that although selection state array 512 is shown to only have one column corresponding to a particular stimulation frame, selection state array 512 may have any number of columns corresponding to any number of stimulation frames as may serve a particular implementation.

In some implementations, sound processor 104 (i.e., channel selection facility 404) may direct a cochlear implant (e.g., cochlear implant 108) included in a cochlear implant system to apply electrical stimulation representative of signals included in the N selected analysis channels to the patient during the stimulation frame by applying stimulation pulses to a plurality of electrodes in accordance with an electrode firing pattern. To this end, implementation 500 may further include a mapping function 514, which may be configured to map the signals (i.e., the signals included in signal array 502) included in the N selected analysis channels to stimulation pulses that are to be applied to the patient via one or more stimulation channels (e.g., via one or more groups of one or more electrodes that define the one or more stimulation channels).

For example, as shown, mapping function 514 may receive the energy signals generated by energy signal generator 504 and the contents of selection state array 512 as inputs. Mapping function 514 may use selection state array 512 to identify the N selected channels, and then use the energy signals that correspond to the N selected analysis channels to define stimulation parameters (e.g., amplitudes, durations, etc.) of the stimulation pulses that are to be applied to the patient in order to present the N selected analysis channels to the patient.

Mapping function 514 may also determine an electrode firing pattern that is to be used to apply the stimulation pulses representative of the signals included in the N selected analysis channels. In some examples, mapping function 514 may incorporate fine structure information into the electrode firing pattern. To this end, as shown in FIG. 5, mapping function 514 may also receive the fine structure signals generated by fine structure signal generator 506 as an input. Mapping function 514 may then use the fine structure signals to determine the electrode firing pattern.

Figure 7:
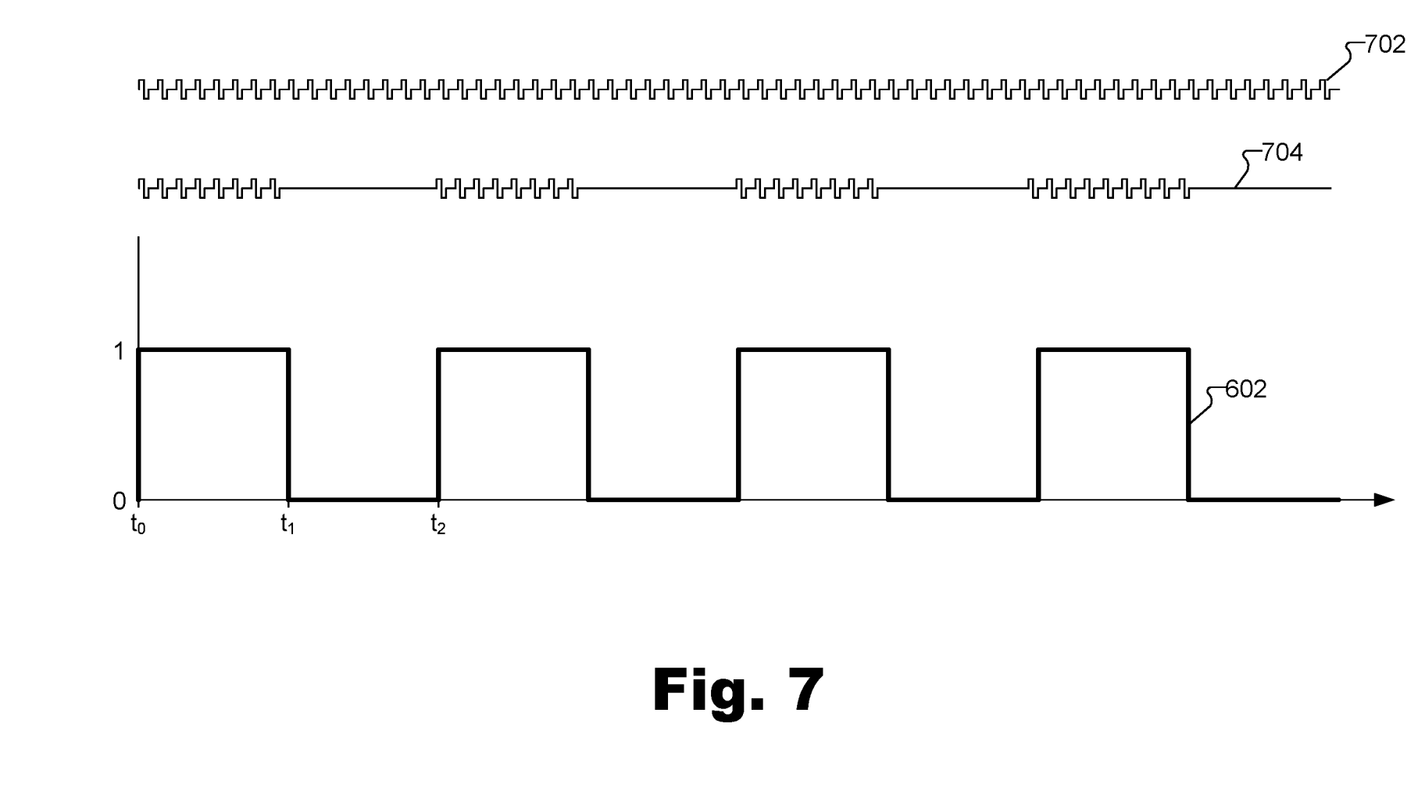
FIG. 7 shows exemplary electrode firing patterns according to principles described herein.

For example, FIG. 7 shows exemplary electrode firing patterns 702 and 704 for a particular analysis channel that corresponds to fine structure signal 602, which is also shown. In this example, fine structure signal 602 is not used to determine electrode firing pattern 702. In contrast, fine structure signal 602 is used to determine electrode firing pattern 704.

As shown, in electrode firing pattern 702, stimulation pulses are repeatedly applied (e.g., once per stimulation frame) in order to deliver information contained within the analysis channel. However, in electrode firing pattern 704, stimulation pulses are only applied during stimulation frames that occur while fine structure signal 602 is equal to one. For example, FIG. 7 shows that in electrode firing pattern 704, stimulation pulses are applied during the time period between $t_0$ and $t_1$, and that stimulation pulses are not applied during the time period between $t_1$ and $t_2$. By modulating electrode firing pattern 704 in this manner, mapping function 514 may facilitate perception by the patient of the fine structure information contained in the analysis channel.

As described above, because the fine structure signals are used to select which analysis channels are to be presented during a particular stimulation frame, the systems and methods described herein may ensure that the analysis channel described in the example of FIG. 7 is not selected for presentation during any of the time periods shown in FIG. 7 in which fine structure signal 602 is equal to zero.

The N-of-M channel selection strategy described in connection with FIG. 5 is merely illustrative of the many different N-of-M channel selection strategies that may be at least in part based on fine structure information. For example, fine structure information may be used in connection with an N-of-M channel selection strategy that employs temporal modification. As used herein, an N-of-M channel selection strategy that employs temporal modification is a channel selection strategy that 1) increases a probability that a particular analysis channel will be selected for presentation during a stimulation frame if the particular analysis channel was not selected during one or more stimulation frames that temporally precede the stimulation frame, and 2) decreases the probability that the particular analysis channel will be selected for presentation during the stimulation frame if the particular analysis channel was selected during the one or more stimulation frames that temporally precede the stimulation frame. By employing temporal modification, this N-of-M channel selection strategy may achieve complete spectral coverage (i.e., ensure that even analysis channels that have relatively low energy levels are still at least occasionally selected for presentation to the patient).

Figure 8:
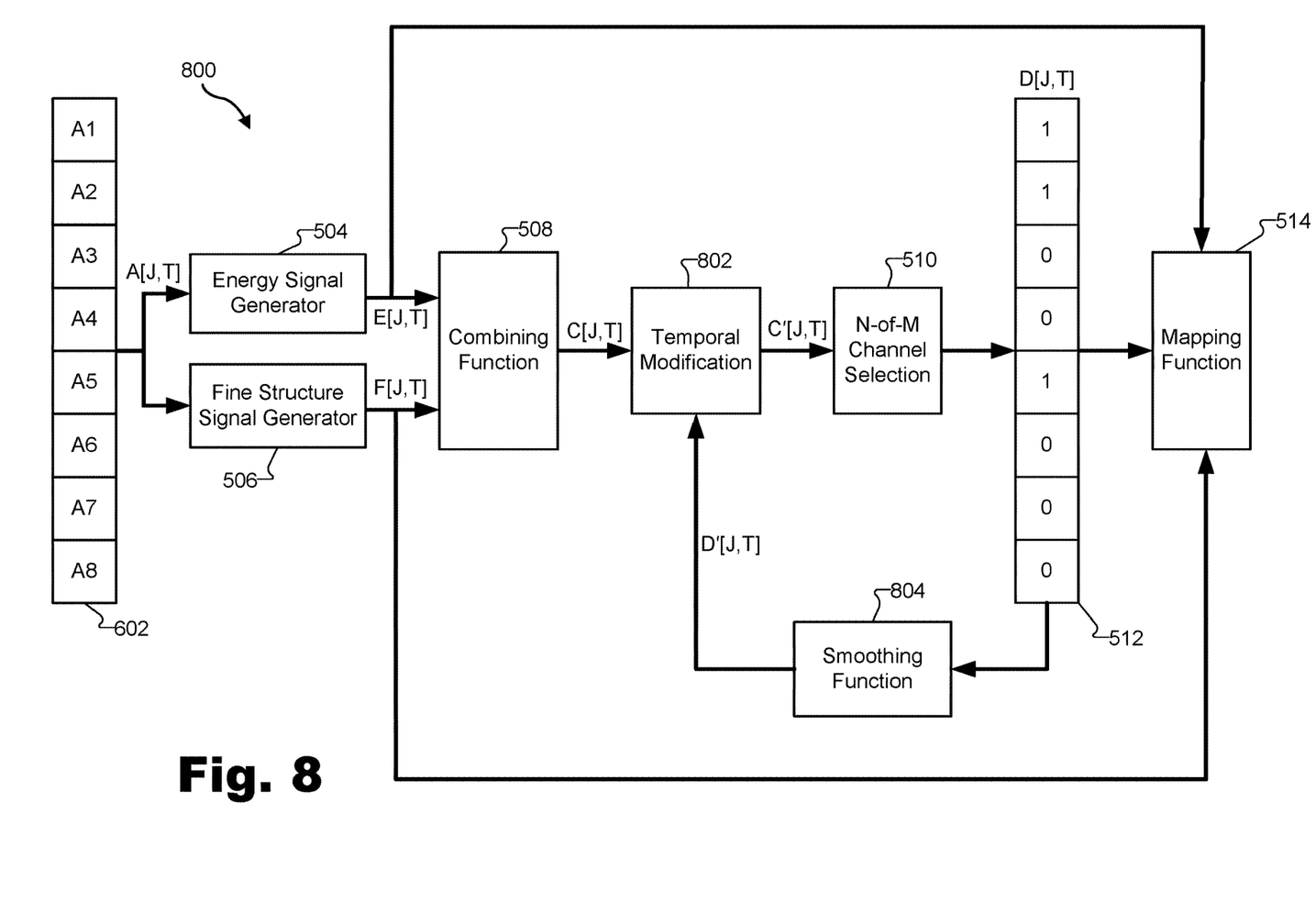
FIG. 8 shows an exemplary implementation of an N-of-M channel selection strategy that employs temporal modification and that utilizes fine structure information according to principles described herein.

FIG. 8 illustrates an exemplary implementation 800 of an N-of-M channel selection strategy that employs temporal modification and that utilizes fine structure information. Implementation 800 is similar to implementation 500, except that implementation 800 further includes a temporal modification block 802 and a smoothing function block 804.

As shown, the selection signals generated by combining function 508 and represented by C[J,T] are input into temporal modification block 802. The contents of the selection state array 512 are also provided as an input to temporal modification block 802. Temporal modification block 802 may modify the selection signals based on whether their corresponding analysis channels have been selected for presentation during one or more stimulation frames that temporally precede the stimulation frame. The modified selection signals are represented by C'[J,T] and, like the selection signals represented by C[J,T], each have an individual value.

Temporal modification block 802 may generate the modified selection signals represented by C'[J,T] in any suitable manner. For example, if temporal modification block 802 determines that a particular analysis channel was not selected for presentation to the patient during one or more stimulation frames that temporally precede the stimulation frame, temporal modification block 802 may increase a value of the modified selection signal corresponding to the particular analysis channel (e.g., by adding gain to the selection signal that corresponds to the particular analysis channel). This may increase the probability that the particular analysis channel will be included in the N analysis channels selected by N-of-M channel selection block 510 for presentation to the patient during the stimulation frame. In some examples, the amount of gain added to the selection signal may vary depending on the particular analysis channel that corresponds to the selection signal. For example, a relatively high amount of gain may be added to selection signals corresponding to analysis channels that would not otherwise be selected very often. These analysis channels may be identified in any suitable manner.

As another example, if temporal modification block 802 determines that a particular analysis channel was selected for presentation to the patient during the one or more stimulation frames that temporally precede the stimulation frame, temporal modification block 802 may decrease a value of the modified selection signal corresponding to the particular analysis channel (e.g., by subtracting gain from the selection signal that corresponds to the particular analysis channel). As will be described below, this may decrease the probability that the particular analysis channel will be included in the N analysis channels selected by N-of-M channel selection block 510 for presentation to the patient during the stimulation frame. In some examples, the amount of gain subtracted from the selection signal may vary depending on the particular analysis channel that corresponds to the selection signal. For example, a relatively low amount of gain may be subtracted from selection signals corresponding to analysis channels that would not otherwise be selected very often. These analysis channels may be identified in any suitable manner.

As shown in FIG. 8, the modification of the selection signals represented by C[J,T] as performed by temporal modification block 802 is recursively based on which analysis channels are selected for presentation to the patient by N-of-M channel selection block 512.

For example, as shown, the output of N-of-M channel selection block 510 is represented by the binary values contained within selection state array 512. As described in reference to FIG. 5 above, these values are mathematically represented by D[J,T]. In the particular example of FIG. 8, a binary value of "1" indicates that an analysis channel has been dropped (i.e., not selected for presentation during the stimulation frame). Conversely, a binary value of "0" indicates that the analysis channel has been selected for presentation during the stimulation frame. Hence, as shown in FIG. 8, there are five "0" values included in selection state array 512, indicating that five analysis channels have been selected for presentation to the patient during the stimulation frame. It will be recognized that although selection state array 512 is shown to only have one column corresponding to a particular stimulation frame, selection state array 512 may have any number of columns corresponding to any number of stimulation frames as may serve a particular implementation.

The contents of selection state array 512 may be output to smoothing function block 804, which may output a smoothed signal represented by D'[J,T] based on the contents of selection state array 512. One of the purposes of smoothing function block 804 is to modify the number of stimulation frames that are taken into account by temporal modification block 802. In some examples, temporal modification block 802 will only take into account a stimulation frame that immediately and temporally precedes the stimulation frame represented by T (i.e., a stimulation frame represented by T−1). In alternative examples, temporal modification block 802 will take into account a plurality of stimulation frames that immediately and temporally precede the stimulation frame. As used herein, if a stimulation frame "immediately and temporally" precedes another stimulation frame, no other stimulation frames are temporally interposed in between the two stimulation frames.

It will be recognized that smoothing function block 804 may alternatively not be included within implementation 800. However, assuming that smoothing function block 804 is included in implementation 800, the modified selection signals output by temporal modification block 802 may be represented by E'[J,T]=E[J,T]+(D'[J,T]−0.5)×G[J], where G[J] represents a user definable amount of gain.

Hence, in accordance with this equation, if, for a particular analysis channel, the signal D'[J,T] is greater than 0.5 (i.e., the analysis channel is dropped for one or more stimulation frames), E'[J,T] will be greater than E[J,T], thus increasing the probability that the particular analysis channel will be selected for presentation during the stimulation frame represented by T. Alternatively, if the signal D'[J,T] is less than 0.5 (i.e., the analysis channel is selected for one or more stimulation frames), E'[J,T] will be less than E[J,T], thus decreasing the probability that the particular analysis channel will be selected for presentation during the stimulation frame represented by T.

Figure 9:
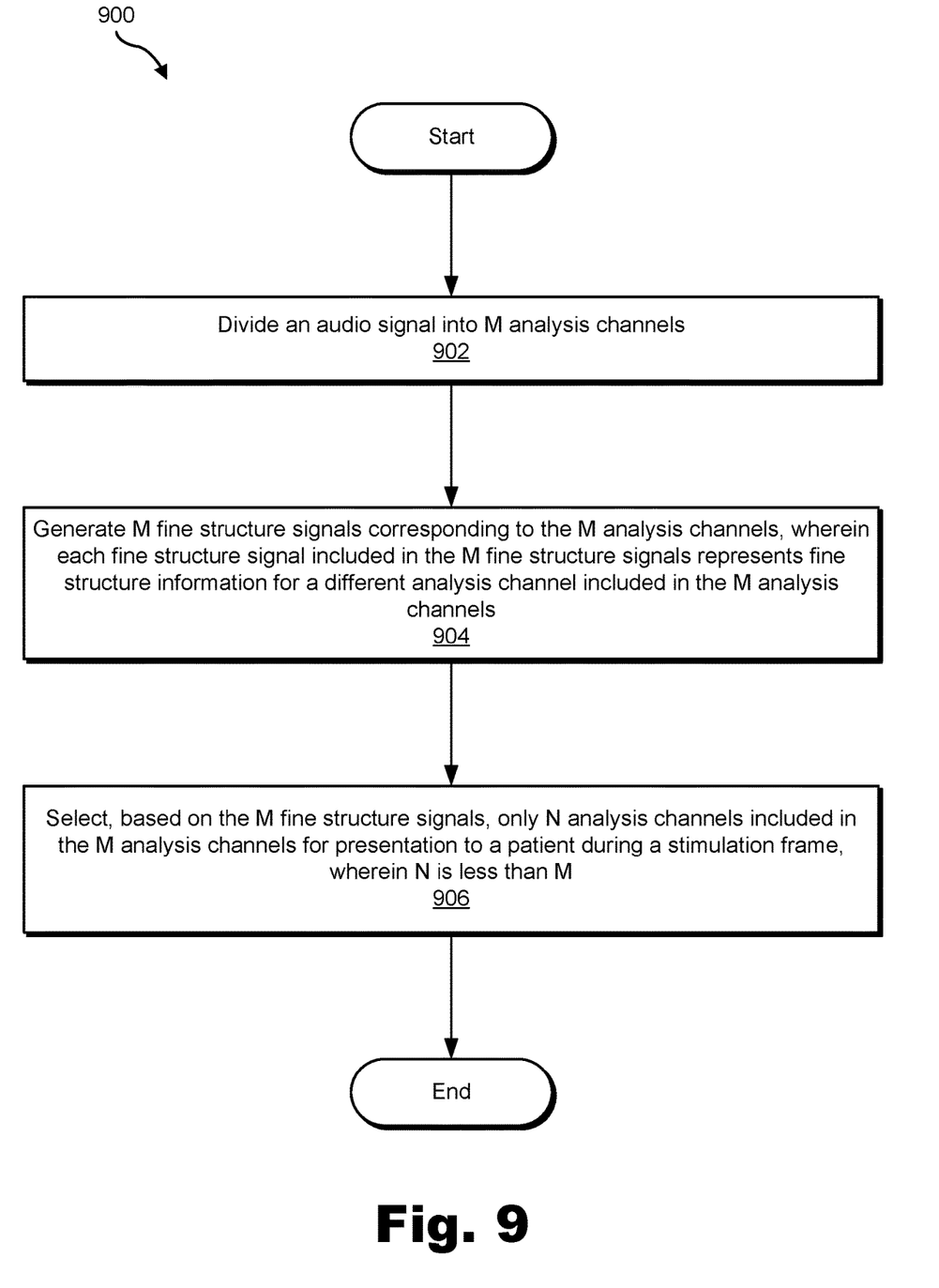
FIG. 9 illustrates an exemplary method according to principles described herein.

FIG. 9 illustrates an exemplary channel selection method 900 that utilizes fine structure information. While FIG. 9 illustrates exemplary operations according to one embodiment, other embodiments may omit, add to, reorder, and/or modify any of the operations shown in FIG. 9. One or more of the operations shown in FIG. 9 may be performed by sound processor 104 and/or any implementation thereof.

In operation 902, a sound processor divides an audio signal into M analysis channels. Operation 902 may be performed in any of the ways described herein.

In operation 904, the sound processor generates M fine structure signals corresponding to the M analysis channels, wherein each fine structure signal included in the M fine structure signals represents fine structure information for a different analysis channel included in the M analysis channels. Operation 904 may be performed in any of the ways described herein.

In operation 906, the sound processor selects, based on the M fine structure signals, only N analysis channels included in the M analysis channels for presentation to a patient during a stimulation frame, wherein N is less than M. Operation 906 may be performed in any of the ways described herein.

The channel-specific gain G[J] may be adjusted to work in combination with the fine structure. For example, in certain implementations, fine structure may be applied only to the low frequency channels. In such a case, the gain may G[J] may be lower (or substantially zero) for the low-frequency channels. In this case, the low frequency fine structure representation will not be reduced.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system associated with a patient and comprising:
  a spectral analysis facility configured to divide an audio signal into M analysis channels; and
  a channel selection facility communicatively coupled to the spectral analysis facility and that is configured to
    generate M fine structure signals corresponding to the M analysis channels, wherein each fine structure signal included in the M fine structure signals represents fine structure information for a different analysis channel included in the M analysis channels, and
    select, based on the M fine structure signals, only N analysis channels included in the M analysis channels for presentation to the patient during a stimulation frame, wherein N is less than M;
  wherein the channel selection facility is configured to generate a fine structure signal corresponding to a particular analysis channel included in the M analysis channels by:
    determining a frequency corresponding to the particular analysis channel; and
    generating a pulse train that has the determined frequency, the pulse train configured to prevent stimulation pulses from being applied via one or more electrodes that correspond to the analysis channel during periods of time that correspond to when the pulse train is equal to zero;
  wherein the pulse train is the fine structure signal corresponding to the particular analysis channel.

2. The sound processor of claim 1, wherein:
the channel selection facility is further configured to generate M energy signals corresponding to the M analysis channels, wherein each energy signal included in the M energy signals represents an energy level within a different analysis channel included in the M analysis channels; and
the selection of the only N analysis channels is further based on the M energy signals.

3. The sound processor of claim 2, wherein the M energy signals are M envelope signals, wherein each envelope signal included in the M envelope signals represents an envelope of a different analysis channel included in the M analysis channels.

4. The sound processor of claim 2, wherein the channel selection facility is configured to select the N analysis channels for presentation to the patient during the stimulation frame by:
generating, based on the M fine structure signals and the M energy signals, M selection signals having individual values and each corresponding to a different analysis channel included in the M analysis channels, wherein each selection signal included in the M selection signals is generated based on a single fine structure signal included in the M fine structure signals and on a single energy signal included in the M energy signals that both correspond to the same analysis channel included in the M analysis channels;
identifying N highest values out of the individual values, the N highest values corresponding to a subset of selection signals included in the M selection signals, the subset of selection signals corresponding to a subset of analysis channels included in the M analysis channels; and
designating the subset of analysis channels that correspond to the subset of selection signals as the N analysis channels that are selected for presentation to the patient during the stimulation frame.

5. The sound processor of claim 4, wherein the generating of the M selection signals comprises generating a particular selection signal included in the M selection signals and that corresponds to a particular analysis channel included in the M analysis channels by combining a fine structure signal corresponding to the particular analysis channel and that is included in the M fine structure signals with an energy signal corresponding to the particular analysis channel and that is included in the M energy signals.

6. The sound processor of claim 1, wherein the determining of the frequency corresponding to the particular analysis channel comprises:
detecting a spectral peak included in the particular analysis channel;
identifying a frequency of the spectral peak; and
designating the identified frequency of the spectral peak as the frequency corresponding to the particular analysis channel.

7. The sound processor of claim 1, wherein the channel selection facility is further configured to direct a cochlear implant included in the cochlear implant system to apply electrical stimulation representative of signals included in the N analysis channels to the patient during the stimulation frame by applying stimulation pulses to a plurality of electrodes in accordance with an electrode firing pattern.

8. The sound processor of claim 7, wherein the channel selection facility is further configured to determine the electrode firing pattern based on the M fine structure signals.

9. The sound processor of claim 1, wherein the generation of the M fine structure signals is based on at least one of:
frequencies of the M analysis channels;
a predetermined stimulation frame rate associated with the stimulation frame; and
channel numbers of the M analysis channels.

10. The sound processor of claim 1, wherein the channel selection facility is further configured to:
increase a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame; and
decrease the probability that the particular analysis channel will be included in the N analysis channels selected for presentation to the patient during the stimulation frame if the particular analysis channel was selected for presentation to the patient during the one or more stimulation frames that temporally precede the stimulation frame.

11. The sound processor of claim 1, wherein M is an integer equal to or greater than eight, and wherein N is an integer that is at least one less than M.

12. The sound processor of claim 1, wherein the audio signal is representative of sound presented to the patient.

13. A system comprising:
a cochlear implant implanted within a patient;
a plurality of electrodes communicatively coupled to the cochlear implant and implanted within a cochlea of the patient; and
a sound processor communicatively coupled to the cochlear implant and that is configured to
divide an audio signal into M analysis channels,
generate M fine structure signals corresponding to the M analysis channels, wherein each fine structure signal included in the M fine structure signals represents fine structure information for a different analysis channel included in the M analysis channels,
generate M energy signals corresponding to the M analysis channels, wherein each energy signal included in the M energy signals represents an energy level within a different analysis channel included in the M analysis channels,
select, based on the generated M fine structure signals and the generated M energy signals, only N analysis channels included in the M analysis channels for presentation to a patient during a stimulation frame, wherein N is less than M,
determine, based on the M fine structure signals, an electrode firing pattern, and
direct the cochlear implant to apply electrical stimulation representative of signals included in the N analysis channels to the patient during the stimulation frame by applying stimulation pulses to the plurality of electrodes in accordance with the determined electrode firing pattern
wherein the sound processor is configured to generate a fine structure signal corresponding to a particular analysis channel included in the M analysis channels by:
determining a frequency corresponding to the particular analysis channel; and
generating a pulse train that has the determined frequency, the pulse train configured to prevent stimulation pulses from being applied via one or more electrodes that correspond to the analysis channel during periods of time that correspond to when the pulse train is equal to zero;

wherein the pulse train is the fine structure signal corresponding to the particular analysis channel.

14. The system of claim 13, wherein the sound processor is configured to select the N analysis channels for presentation to the patient during the stimulation frame by:

generating, based on the M fine structure signals and the M energy signals, M selection signals having individual values and each corresponding to a different analysis channel included in the M analysis channels, wherein each selection signal included in the M selection signals is generated based on a single fine structure signal included in the M fine structure signals and on a single energy signal included in the M energy signals that both correspond to the same analysis channel included in the M analysis channels;

identifying N highest values out of the individual values, the N highest values corresponding to a subset of selection signals included in the M selection signals, the subset of selection signals corresponding to a subset of analysis channels included in the M analysis channels; and designating the subset of analysis channels that correspond to the subset of selection signals as the N analysis channels that are selected for presentation to the patient during the stimulation frame.

15. A method comprising:

dividing, by a sound processor included in a cochlear implant system associated with a patient, an audio signal into M analysis channels;

generating, by the sound processor, M fine structure signals corresponding to the M analysis channels, wherein each fine structure signal included in the M fine structure signals represents fine structure information for a different analysis channel included in the M analysis channels; and selecting, by the sound processor and based on the M fine structure signals, only N analysis channels included in the M analysis channels for presentation to the patient during a stimulation frame, wherein N is less than M;

wherein the generating of a fine structure signal corresponding to a particular analysis channel included in the M analysis channels comprises:

determining a frequency corresponding to the particular analysis channel; and generating a pulse train that has the determined frequency, the pulse train configured to prevent stimulation pulses from being applied via one or more electrodes that correspond to the analysis channel during periods of time that correspond to when the pulse train is equal to zero;

wherein the pulse train is the fine structure signal corresponding to the particular analysis channel.

16. The method of claim 15, further comprising generating, by the sound processor, M energy signals corresponding to the M analysis channels, wherein each energy signal included in the M energy signals represents an energy level within a different analysis channel included in the M analysis channels;

wherein the selecting of the only N analysis channels is further based on the M energy signals.

17. The method of claim 16, wherein the selecting or the N analysis channels for presentation to the patient during the stimulation frame comprises:

generating, based on the M fine structure signals and the M energy signals, M selection signals having individual values and each corresponding to a different analysis channel included in the M analysis channels, wherein each selection signal included in the M selection signals is generated based on a single fine structure signal included in the M fine structure signals and on a single energy signal included in the M energy signals that both correspond to the same analysis channel included in the M analysis channels;

identifying N highest values out of the individual values, the N highest values corresponding to a subset of selection signals included in the M selection signals, the subset of selection signals corresponding to a subset of analysis channels included in the M analysis channels; and designating the subset of analysis channels that correspond to the subset of selection signals as the N analysis channels that are selected for presentation to the patient during the stimulation frame.

* * * * *